(12) United States Patent
Desos et al.

(10) Patent No.: US 7,262,191 B2
(45) Date of Patent: Aug. 28, 2007

(54) BENZOTHIADIAZINE COMPOUNDS

(75) Inventors: Patrice Desos, Bois-Colombes (FR); Alexis Cordi, Suresnes (FR); Pierre Lestage, La Celle-Saint Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/266,072

(22) Filed: Nov. 3, 2005

(65) Prior Publication Data

US 2006/0094713 A1 May 4, 2006

(30) Foreign Application Priority Data

Nov. 3, 2004 (FR) .................................. 04 11691

(51) Int. Cl.
*C07D 285/22* (2006.01)
*A61K 31/5415* (2006.01)
*A61P 25/24* (2006.01)

(52) U.S. Cl. ..................... 514/223.2; 544/12
(58) Field of Classification Search .................. 544/12; 514/223.2
See application file for complete search history.

(56) References Cited

OTHER PUBLICATIONS

Alt et al. Current Pharmaceutical Design, 2005, 11, 1511-1527.*
Black et al. Psychopharmacology (2005) 179: 154-163.*
Maskell, et al., *Br. J. Pharmacol*, 2003, 140, 1313-1319.
Aracava, et al., *JPET*, 2005, 312, 1195-1250.
Advokat, et al., *Neurosci. Biobehav. Rev.*, 1992, 16, 13-24.
Danysz, et al., *Behav. Pharmacol.*, 1995, 6, 455-474.
Lynch, *Neurobiology of Learning and Memory*, 1998, 70, 82-100.
Robbins, et al., *TRENDS in Pharmacological Sciences*, 2006, 27 (3), 141-148.
Bliss, et al., *Nature*, 1993, 361, 31-39.
Ito, et al., *Journal of Physiology*, 1990, 424, 533-543.
Cumin, et al., *Psychopharmacology*, 1982, 78, 104-111.
Arai, et al., *Brain Res.*, 1994, 638, 343-346.
Miu, et al., *Neuropharmacol.*, 2001, 40, 976-983.
Staubli, et al., *Proc. Natl. Acad. Sci.*, 1994, 91, 777-781.
Lebrun, et al., *European Journal of Pharmacology*, 2000, 401, 205-212.
Rao, et al., *Neuroscience Letters*, 2001, 298, 183-186.
Thompson, et al., *Proc. Natl. Acad. Sci.*, 1995, 92, 7667-7671.
Buccafusco, et al., *Neuropharmacol.*, 2004, 46, 10-22.
Porrino, et al., *PLOS Biology*, 2005, 3 (9), 1639-1652.
Ingvar, et al., *Exp. Neurol.*, 1997, 146, 553-559.
Lynch, et al., *Exp. Neurol.*, 1997, 145, 89-92.
Baudry, *Neurobiology of Learning and Memory*, 2001, 76, 284-297.
Day, et al., *Nature*, 2003, 424, 205-209.
Lynch, *Current Opinion in Pharmacology*, 2006, 6, 82-88.
Lin, et al., *Brain Research*, 2002, 955, 164-173.
Desai, et al., *Neuropharmacology*, 1995, 34 (2), 141-147.
Lockhart, et al., *European Journal of Pharmacology*, 2000, 401, 145-153.
Jhee, et al., *J. Clin. Pharmacol.*, 2006, 46, 424-432.
Roger, et al., *Soc. Neurosci. Abstr.*, 2004, Abstract No. 219.11.
Dicou, et al., *Brain Research*, 2003, 970, 221-225.
Bahr, et al., *Exp. Neurol.*, 2002, 174, 37-47.
Murray, et al., *JPET*, 2003, 306, 752-762.
O'Neill, et al., *European Journal of Pharmacology*, 2004, 486, 163-174.
O'Neill, et al., *CNS Drug Rev.*, 2005, 11 (1), 77-96.
Bai, et al., *Neuropharmacology*, 2003, 44, 1013-1021.
Lauterborn, et al., *J. of Neuroscience*, 2000, 20 (1), 8-21.
Carrie, et al., *Soc. Neurosci. Abstr.*, 2005, Abstract No. 1018.4.
Lockhart, et al., *Soc. Neurosci. Abstr.*, 2004, Abstract No. 92.12.
Munoz, et al., *Soc. Neurosci. Abstr.*, 2004, Abstract No. 85.13.
Nibuya, et al., *J. of Neuroscience*, 1995, 15(11), 7539-7547.
Dias, et al., *Neuropharmacology*, 2003, 45, 553-563.
Alt, et al., *Curr. Pharm. Des.*, 2005, 11 (12), 1511-1527.
Alt, et al., *Biochemical Pharmacology*, 2006, 71, 1273-1288.
Nakamura, et al., *Psychopharmacology*, 2001, 158, 205-212.
Li, et al., *Neuropharmacology*, 2001, 40, 1028-1033.
Knapp, et al., *European Journal of Pharmacology*, 2002, 440, 27-35.

* cited by examiner

*Primary Examiner*—Kahsay Habte
(74) *Attorney, Agent, or Firm*—Hueschen and Sage

(57) ABSTRACT

The invention relates to compounds of formula (I):

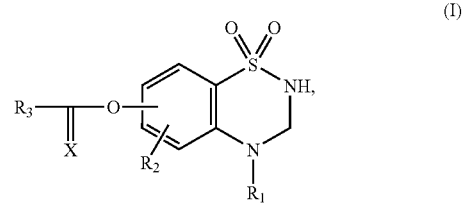

wherein:
X represents oxygen or sulphur,
$R_1$ represents linear or branched ($C_1$-$C_6$)alkyl substituted by one or more halogen atoms,
$R_2$ represents hydrogen, halogen or hydroxy,
$R_3$ represents a group $R_4$ or —Y—$R_5$ wherein $R_4$, Y and $R_5$ are as defined in the description,
and medicinal products containing the same which are useful in treating or preventing disorders associated with AMPA flux.

11 Claims, No Drawings

BENZOTHIADIAZINE COMPOUNDS

FIELD OF THE INVENTION

The present invention relates to new benzothiadiazine compounds. The compounds of the present invention are new and have very valuable pharmacologic characteristics as AMPA modulators.

BACKGROUND OF THE INVENTION

It has now been recognised that the excitatory amino acids, very especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral Reviews, 1992, 16, 13-24; Progress in Neurobiology, 1992, 39, 517-545).

In addition, innumerable works have in recent years demonstrated the existence of sub-types of excitatory amino acid receptors and their functional interactions (Molecular Neuropharmacology, 1992, 2, 15-31).

Among those receptors, the AMPA α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (Journal of Neurochemistry, 1992, 58, 1199-1204).

DESCRIPTION OF THE PRIOR ART

In the literature, compounds having a benzamide structure have been described as possessing this same mechanism of action and as improving memory performance (Synapse, 1993, 15, 326-329). Compound BA 74, in particular, is the most active of those new pharmacological agents.

Finally, the patent specification EP 692 484 describes a benzothiadiazine compound having facilitating activity on the AMPA current, and the patent application WO 99/42456 describes, inter alia, certain benzothiadiazine compounds as modulators of AMPA receptors.

The benzothiadiazine compounds to which the present invention relates, besides being new, surprisingly exhibit especially valuable pharmacological activity on the AMPA current. They are useful as AMPA modulators for the treatment or prevention of disorders of memory and cognition that are associated with age, with syndromes of anxiety or depression, with progressive neurodegenerative diseases, with Alzheimer's disease, with Pick's disease, with Huntington's chorea, with schizophrenia, with the sequelae of acute neurodegenerative diseases, with the sequelae of ischaemia and with the sequelae of epilepsy.

DETAILED DESCRIPTION OF THE INVENTION

More specifically, the present invention relates to compounds of formula (I):

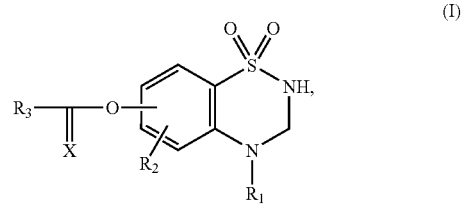

wherein:

X represents an oxygen or sulphur atom, $R_1$ represents a linear or branched ($C_1$-$C_6$)alkyl group substituted by one or more halogen atoms, $R_2$ represents a hydrogen atom, a halogen atom or a hydroxy group, $R_3$ represents a group $R_4$ or —Y—$R_5$ wherein $R_4$ represents a linear or branched ($C_1$-$C_6$)alkyl group optionally substituted by an aryl group; a linear or branched ($C_2$-$C_6$)alkenyl group optionally substituted by an aryl group; a linear or branched ($C_1$-$C_6$)polyhaloalkyl group; a ($C_3$-$C_7$)cycloalkyl group an adamantyl group; an aryl group; or a heteroaryl group, Y represents an oxygen or sulphur atom or an NR group wherein R represents a hydrogen atom or a linear or branched ($C_1$-$C_6$)alkyl group, and $R_5$ may take any of the meanings of $R_4$, to their enantiomers and diastereoisomers, and also to addition salts thereof with a pharmaceutically acceptable acid or base, it being understood that:

an aryl group means a monocyclic aromatic group or a bicyclic group in which at least one of the rings is aromatic, optionally substituted by one or more identical or different groups selected from halogen, linear or branched ($C_1$-$C_6$)alkyl, linear or branched ($C_1$-$C_6$)alkoxy, linear or branched ($C_1$-$C_6$)polyhaloalkyl, linear or branched ($C_1$-$C_6$)polyhaloalkoxy, hydroxy, cyano, nitro, amino (optionally substituted by one or more identical or different groups selected from linear or branched ($C_1$-$C_6$)alkyl and linear or branched ($C_1$-$C_6$) acyl), ($C_1$-$C_6$)alkylsulphonylamino and phenyl (optionally substituted by one or more identical or different groups selected from halogen, linear or branched ($C_1$-$C_6$)alkyl, linear or branched ($C_1$-$C_6$)polyhaloalkyl, hydroxy and linear or branched ($C_1$-$C_6$)alkoxy), a heteroaryl group means a monocyclic aromatic group or a bicyclic group in which at least one of the rings is aromatic, containing one, two or three identical or different hetero atoms selected from nitrogen, oxygen and sulphur, optionally substituted by one or more identical or different groups selected from halogen, linear or branched ($C_1$-$C_6$)alkyl, linear or branched ($C_1$-$C_6$)alkoxy, linear or branched ($C_1$-$C_6$)polyhaloalkyl, linear or branched ($C_1$-$C_6$)polyhaloalkoxy, hydroxy, cyano, nitro, amino (optionally substituted by one or more identical or different groups selected from linear or branched ($C_1$-$C_6$)alkyl and linear or branched ($C_1$-$C_6$)acyl) and ($C_1$-$C_6$)alkyl-sulphonylamino.

Greater preference is given to X representing an oxygen atom.

Preference is given to the group $R_1$ being haloethyl such as, for example, fluoroethyl, chloroethyl or bromoethyl.

$R_2$ advantageously represents a hydrogen atom.

Preference is given to the group $R_3$ being an aryl or heteroaryl group.

More specifically, the invention relates to compounds of formula (I) which are:

4-(2-fluoroethyl)-1,1-dioxido-3,4-dihydro-2H-1,2,4-benzothiadiazin-7-yl 3-thiophenecarboxylate, and 4-(2-fluoroethyl)-1,1-dioxido-3,4-dihydro-2H-1,2,4-benzothiadiazin-7-yl benzoate.

The invention relates also to a process for the synthesis of compounds of formula (I), which process is characterised in that there is used as starting material the compound of formula (II):

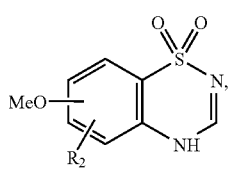

(II)

wherein $R_2$ is as defined for formula (I), with which there is condensed, in a basic medium, a linear or branched ($C_1$-$C_6$) haloalkyl bearing an hydroxy group:

which is then converted into a corresponding halogenated compound to yield compound of formula (III):

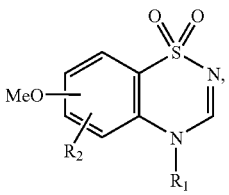

(III)

wherein $R_1$ and $R_2$ are as defined for formula (I), which is subjected to reduction, in the presence of $NaBH_4$, for example, to obtain the compound of formula (IV):

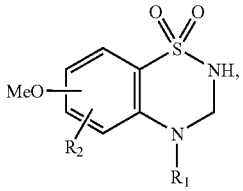

(IV)

wherein $R_1$ and $R_2$ are as defined hereinbefore, which is subjected to a demethylation reaction, in the presence of $BBr_3$ or $BF_3$, for example, to yield the compound of formula (V):

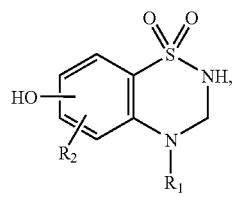

(V)

wherein $R_1$ and $R_2$ are as defined hereinbefore, which compound of formula (V) may also be obtained by starting from the compound of formula (III), which is subjected to a demethylation reaction, in the presence of $BBr_3$ or $BF_3$, for example, to yield the compound of formula (VI):

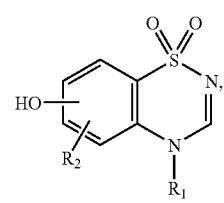

(VI)

wherein $R_1$ and $R_2$ are as defined hereinbefore, which is subjected to reduction, in the presence of $NaBH_4$, for example, to obtain the compound of formula (V) as defined hereinbefore, with which there is condensed the compound of formula (VII):

(VII)

wherein $R_3$ is as defined for formula (I), to obtain the compound of formula (I/a), a particular case of the compounds of formula (I):

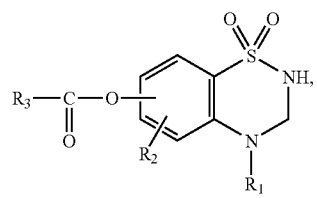

(I/a)

wherein $R_1$, $R_2$ and $R_3$ are as defined hereinbefore, which is subjected to a thionating agent, such as Lawesson's reagent, for example, to yield the compound of formula (I/b), a particular case of the compounds of formula (I):

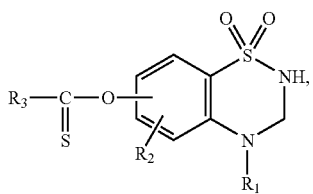

wherein $R_1$, $R_2$ and $R_3$ are as defined hereinbefore, the compounds of formulae (I/a) and (I/b) forming the totality of the compounds of formula (I), which are purified, if necessary, according to a conventional purification technique, are separated, where appropriate, into their isomers according to a conventional separation technique and are converted, if desired, into their addition salts with a pharmaceutically acceptable acid or base.

The invention relates also to the compound of formula (V):

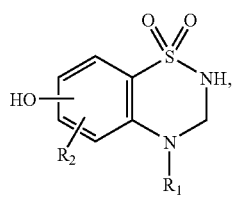

as defined hereinbefore, which is useful as a synthesis intermediate for the synthesis of compounds of formula (I) and is useful as an AMPA receptor modulating agent, and more especially to the compound of formula (VIII), a particular case of compounds of formula (V):

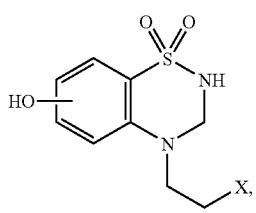

wherein X represents a fluorine, chlorine, bromine or iodine atom, which is useful as a synthesis intermediate for the synthesis of compounds of formula (I) and is useful as an AMPA receptor modulating agent.

The invention relates also to pharmaceutical compositions comprising, as active ingredient, a compound of formula (I) with one or more appropriate, inert, non-toxic excipients.

Among the pharmaceutical compositions according to the invention there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and the age and weight of the patient and ranges from 1 to 500 mg per day in one or more administrations.

The Preparations and Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry, . . . ).

Preparation 1: 4-(2-Bromoethyl)-3,4-dihydro-2H-1,2,4-benzothiadiazin-7-ol 1,1-dioxide Step A: 2-(7-Methoxy-1,1-dioxido-4H-1,2,4-benzothiadiazin-4-yl)ethanol To a solution of 7-methoxy-4H-1,2,4-benzothiadiazine 1,1-dioxide (4.0 g, 18.8 mmol) in a mixture of 30 ml of DMF and 30 ml of $CH_3CN$ there are added 8.6 g (56.6 mmol) of CsF and 1.47 ml (18.8 mmol) of 2-bromoethanol. Stirring is carried out for 2 hours at 75° C. and 1.47 ml (18.8 mmol) of 2-bromoethanol are added. After 6 more hours at 75° C., a further 1.47 ml (18.8 mmol) of 2-bromoethanol and then 2.8 g (18.8 mmol) of CsF are added and stirring is continued at 75° C. overnight. The salts are filtered off at ambient temperature and rinsed with $CH_3CN$; the filtrate is evaporated to dryness. The residue is taken up in $CH_2Cl_2$, and the organic phase is washed with saturated NaCl solution and dried ($MgSO_4$). After evaporation, the sticky residue is taken up in a mixture of ethyl ether/$CH_2Cl_2$. The gum is triturated until a solid is obtained, which is filtered off to obtain the title compound.

Melting point: 160-162° C.

Elemental Microanalysis:

|  | C | H | N | S |
| --- | --- | --- | --- | --- |
| theoretical % | 46.87 | 4.72 | 10.93 | 12.51 |
| experimental % | 46.99 | 4.96 | 10.34 | 12.51 |

Step B: 4-(2-Fluoroethyl)-7-methoxy-4H-1,2,4-benzothiadiazine 1,1-dioxide

To a solution of 3.85 g (15.02 mmol) of the compound of the previous Step in 100 ml of $CH_2Cl_2$, cooled in an ice bath, there are added, dropwise, 3.97 ml (30.0 mmol) of DAST diluted with 20 ml of $CH_2Cl_2$. The reaction solution is then allowed to return to ambient temperature in about 1 hour; 100 ml of saturated NaCl solution are then poured in and the organic phase is decanted off, dried ($MgSO_4$) and evaporated in vacuo. The residue is triturated in a mixture of ethyl ether/$CH_2Cl_2$ until a solid is obtained which is filtered off to obtain the title compound.

Melting point: 123-128° C.

Elemental Microanalysis:

|  | C | H | N | S |
| --- | --- | --- | --- | --- |
| theoretical % | 46.50 | 4.29 | 10.85 | 12.42 |
| experimental % | 45.88 | 4.41 | 10.46 | 12.61 |

Step C: 4(2-Fluoroethyl)-7-methoxy-3,4-dihydro-2H-1,2,4-benzothiadiazine 1,1-dioxide 454 mg (12.0 mmol) of NaBH$_4$, in small portions, are added to a suspension of 2.77 g (10.7 mmol) of the compound of the previous Step in 25 ml of ethanol. After stirring for 2 hours at ambient temperature, 1N HCl is added dropwise until a white precipitate forms which is filtered off in order to recover the title compound.
Melting point: 91-93° C.

Step D: 4-(2-Bromoethyl)-3,4-dihydro-2H-1,2,4-benzothiadiazin-7-ol 1,1-dioxide 17.6 ml (17.6 mmol) of a 1M solution of BBr$_3$ in CH$_2$Cl$_2$ are added, dropwise, to a solution of 1.53 g (5.88 mmol) of the compound of the previous Step in 70 ml of CH$_2$Cl$_2$, cooled in an ice bath. The mixture is stirred overnight while being allowed to return to ambient temperature. The reaction suspension is cooled in an ice bath and 50 ml of water are added dropwise. After stirring for 30 minutes, the precipitate is filtered off, rinsed with water and dried in vacuo. The expected compound is accordingly obtained in the form of a light brown powder.
Melting point: 144-148° C.

Preparation 2: 4-(2-Fluoroethyl)-3,4-dihydro-2H-1,2,4-benzothiadiazin-7-ol 1,1-dioxide Step A:
4-(2-Fluoroethyl)-4H-1,2,4-benzothiadiazin-7-ol 1,1-dioxide 100 ml (950 mmol) of the complex BF$_3$.Me$_3$S are introduced into a two-necked flask purged with nitrogen and connected to a trap containing sodium hypochlorite solution, by means of a cannula and under nitrogen pressure. Whilst stirring and under a gentle current of nitrogen there is then quickly added, in small portions, a suspension of 5.63 g (21.8 mmol) of the compound of Step B of Preparation 1 in 75 ml of CH$_2$Cl$_2$. The current of nitrogen is stopped and the reaction suspension is stirred overnight at ambient temperature. The reaction mixture is cooled in an ice bath, and ice and water are added. The suspension is stirred for 30 minutes, and the precipitate is filtered off and rinsed with water and with heptane. The solid is dried and recrystallised from water to yield the title compound.
Melting point: 230-235° C.
Elemental Microanalysis:

|  | C | H | N | S |
|---|---|---|---|---|
| theoretical % | 44.26 | 3.71 | 11.47 | 13.13 |
| experimental % | 44.55 | 4.18 | 11.34 | 13.59 |

Step B: 4-(2-Fluoroethyl)-3,4-dihydro-2H-1,2,4-benzothiadiazin-7-ol 1,1-dioxide

Conditions and treatment identical to Step C of Preparation 1, except that the expected compound is not precipitated after addition of 1N HCl but is extracted with CH$_2$Cl$_2$.
Melting point: 178-180° C.
Elemental Microanalysis:

|  | C | H | N | S |
|---|---|---|---|---|
| theoretical % | 43.90 | 4.50 | 11.38 | 13.02 |
| experimental % | 43.73 | 4.37 | 11.10 | 12.80 |

Preparation 3: 4-(2-Chloroethyl)-3,4-dihydro-2H-1,2,4-benzothiadiazin-7-ol 1,1-dioxide Step A: 4-(2-Chloroethyl)-7-methoxy-4H-1,2,4-benzothiadiazine 1,1-dioxide To a suspension of 1.0 g (3.90 mmol) of the compound of Step A of Preparation 1 in 20 ml of CH$_2$Cl$_2$ there are added, at ambient temperature, 0.1 ml of DMF and then, dropwise, a solution containing 1.42 ml (19.5 mmol) of SOCl$_2$ in 5 ml of CH$_2$Cl$_2$. At the end of the addition, a solution is obtained which is stirred at the reflux of CH$_2$Cl$_2$ for 2 hours. The CH$_2$Cl$_2$ is evaporated off in vacuo and the residue is taken up in a 5% solution of NaHCO$_3$. After trituration of the residue, a solid is obtained which is filtered off, rinsed with water and dried to yield the title compound.
Melting point: 126-130° C.
Elemental Microanalysis:

|  | C | H | N | S |
|---|---|---|---|---|
| theoretical % | 43.72 | 4.04 | 10.20 | 11.67 |
| experimental % | 43.79 | 4.06 | 9.84 | 12.01 |

Step B: 4-(2-Chloroethyl)-7-methoxy-3,4-dihydro-2H-1,2,4-benzothiadiazine 1,1-dioxide Conditions and treatment identical to Step C of Preparation 1.
Melting point: 139-143° C.
Elemental Microanalysis:

|  | C | H | N | S | Cl |
|---|---|---|---|---|---|
| theoretical % | 43.40 | 4.73 | 10.12 | 11.59 | 12.81 |
| experimental % | 43.73 | 5.05 | 9.89 | 11.07 | 13.30 |

Step C: 4-(2-Chloroethyl)-3,4-dihydro-2H-1,2,4-benzothiadiazin-7-ol 1,1-dioxide

Conditions and treatment identical to Step D of Preparation 1.

EXAMPLE 1

4-(2-Fluoroethyl)-1,1-dioxido-3,4-dihydro-2H-1,2,4-benzothiadiazin-7-yl 3-thiophenecarboxylate To a solution of the compound obtained in Preparation 2 (200 mg, 0.812 mmol) in 25 ml of CH$_2$Cl$_2$ there are added 228 µl (1.62 mmol) of Et$_3$N and then, dropwise, a solution of thiophene-3-carboxylic acid chloride in 10 ml of CH$_2$Cl$_2$. The reaction solution is stirred for 2 hours at ambient temperature. 20 ml of 1N HCl are added, and the organic phase is decanted off, dried (MgSO$_4$) and evaporated in vacuo. The residue is chromatographed on silica (CH$_2$Cl$_2$/MeOH 98/2) to yield the title compound.

Melting point: 183° C.

Elemental Microanalysis:

|  | C | H | N | S |
|---|---|---|---|---|
| theoretical % | 47.18 | 3.68 | 7.86 | 17.99 |
| experimental % | 46.91 | 3.85 | 7.62 | 18.20 |

EXAMPLE 2

4-(2-Fluoroethyl)-1,1-dioxido-3,4-dihydro-2H-1,2,4-benzothiadiazin-7-yl benzoate The procedure is as in Example 1, starting from the compound obtained in Preparation 2 and benzoic acid chloride.

Melting point: 145° C.

Elemental Microanalysis:

|  | C | H | N | S |
|---|---|---|---|---|
| theoretical % | 54.85 | 4.32 | 8.00 | 9.15 |
| experimental % | 54.93 | 4.42 | 7.74 | 9.12 |

Pharmacological Study of Compounds of the Invention

Study of the Excitatory Currents Induced by AMPA in *Xenopus* Oocytes a—Method:

mRNA's are prepared from cerebral cortex of male Wistar rats by the guanidinium thiocyanate/phenol/chloroform method. The poly (A$^+$) mRNA's are isolated by chromatography on oligo-dT cellulose and injected at a level of 50 ng per oocyte. The oocytes are incubated for 2 to 3 days at 18° C. to permit expression of the receptors and are then stored at 8-10° C.

Electrophysiological recording is carried out in a Plexiglass® chamber at 20-24° C. in OR2 medium (J. Exp. Zool., 1973, 184, 321-334) by the "voltage-clamp" method using two electrodes, with a third electrode placed in the bath serving as reference.

All the compounds are applied via the incubation medium and the electric current is measured at the end of the application period. AMPA is used in a concentration of 10 μM. For each compound studied, the concentration that doubles (EC2×) or quintuples (EC5×) the intensity of the current induced by AMPA alone (5 to 50 nA) is determined.

b—Results:

The compounds of the invention potentiate the excitatory effects of AMPA to a very considerable degree and their activity is very clearly superior to that of compounds of reference.

By way of example, the compound of Example 1 has an EC2× of 8.0 μM.

Pharmaceutical Composition

Formula for the preparation of 1000 tablets each containing 100 mg of 4-(2-fluoroethyl-1,1-dioxido-3,4-dihydro-2H-1,2,4-benzothiadiazin-7-yl) 3-thiophenecarboxylate (Example 1) . . . 100 g Hydroxypropylcellulose 2 g Wheat starch . . . 10 g Lactose . . . 100 g Magnesium stearate . . . 3 g Talc . . . 3 g

What is claimed is:

1. A compound selected from those of formula (I):

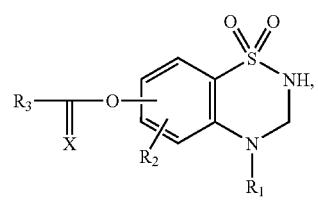

(I)

wherein:
X represents oxygen or sulphur,
R$_1$ represents linear or branched (C$_1$-C$_6$)alkyl substituted by one or more halogen atoms,
R$_2$ represents hydrogen, halogen or hydroxy,
R$_3$ represents a group R$_4$ or —Y—R$_5$ wherein
R$_4$ represents linear or branched (C$_1$-C$_6$)alkyl optionally substituted by aryl; linear or branched (C$_2$-C$_6$)alkenyl optionally substituted by aryl; linear or branched (C$_1$-C$_6$) polyhaloalkyl; (C$_3$-C$_7$)cycloalkyl; adamantly; aryl; or heteroaryl,
Y represents oxygen, sulphur, or NR, wherein R represents hydrogen or linear or branched (C$_1$-C$_6$)alkyl, and R$_5$ may take any of the meanings of R$_4$,
its enantiomers and diastereoisomers, and addition salts thereof with a pharmaceutically acceptable acid or base.

2. A compound of claim 1, wherein X represents oxygen.

3. A compound of claim 1, wherein R$_1$ represents haloethyl.

4. A compound of claim 1, wherein R$_2$ represents hydrogen.

5. A compound of claim 1, wherein R$_3$ represents aryl.

6. A compound of claim 1, wherein R$_3$ represents heteroaryl.

7. A compound of claim 1, which is selected from:
4-(2-fluoroethyl)-1,1-dioxido-3,4-dihydro-2H-1,2,4-benzothiadiazin-7-yl 3-thiophene carboxylate and
4-(2-fluoroethyl)-1,1-dioxido-3,4-dihydro-2H-1,2,4-benzothiadiazin-7-yl benzoate, and addition salts thereof with a pharmaceutically acceptable acid or base.

8. A compound selected form those of formula (V):

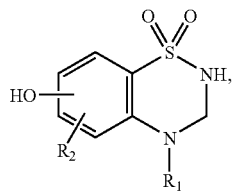
(V)

wherein $R_1$ represents linear or branched ($C_1$-$C_6$) alkyl substituted by one or more halogen atoms and $R_2$ represents hydrogen, halogen or hydroxy.

9. A compound selected form those of formula (VIII):

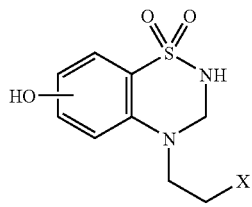
(VIII)

wherein X represents a fluorine, chlorine, bromine or iodine atom.

10. A pharmaceutical composition comprising as active principle an effective amount of a compound of claim 1, together with one or more pharmaceutically acceptable excipients or vehicles.

11. A method for treating a living animal body, including a human, afflicted with a condition selected from anxiety and depression, comprising the step of administering to the living animal body, including a human, an amount of a compound of claim 1, which is effective for alleviation of the condition.

* * * * *

UNITED STATES PATENT AND TRADEMARK OFFICE
CERTIFICATE OF CORRECTION

PATENT NO. : 7,262,191 B2 Page 1 of 1
APPLICATION NO. : 11/266072
DATED : August 28, 2007
INVENTOR(S) : Patrice Desos et al.

It is certified that error appears in the above-identified patent and that said Letters Patent is hereby corrected as shown below:

Cover Page, Assignee: "Les Laboratoires Server" should be --Les Laboratoires Servier--.

Signed and Sealed this

Twenty-seventh Day of November, 2007

JON W. DUDAS
*Director of the United States Patent and Trademark Office*